US012797307B2

(12) United States Patent
Ji et al.

(10) Patent No.: US 12,797,307 B2
(45) Date of Patent: Nov. 17, 2026

(54) COSMETIC COMPOSITION FOR MOLDING, COMPRISING CALCINED LAYERED DOUBLE HYDROXIDE AND POLYMER

(71) Applicant: H&A PHARMACHEM CO., LTD, Gyeonggi-do (KR)

(72) Inventors: Hong Geun Ji, Gyeonggi-do (KR); Young Ah Park, Incheon (KR); Yu Jin Kang, Gyeonggi-do (KR); Ja Inn Kim, Gyeonggi-do (KR); Jong Hyeon Lee, Gyeonggi-do (KR)

(73) Assignee: H&A PHARMACHEM CO., LTD, Gyeonggi-do (KR)

( * ) Notice: Subject to any disclaimer, the term of this patent is extended or adjusted under 35 U.S.C. 154(b) by 663 days.

(21) Appl. No.: 17/603,376

(22) PCT Filed: Apr. 20, 2020

(86) PCT No.: PCT/KR2020/005198

§ 371 (c)(1),
(2) Date: Oct. 13, 2021

(87) PCT Pub. No.: WO2020/218787

PCT Pub. Date: Oct. 29, 2020

(65) Prior Publication Data

US 2022/0211589 A1 Jul. 7, 2022

(30) Foreign Application Priority Data

Apr. 23, 2019 (KR) ........................ 10-2019-0047252

(51) Int. Cl.

| | |
|---|---|
| ***A61Q 19/00*** | (2006.01) |
| ***A61K 8/02*** | (2006.01) |
| ***A61K 8/19*** | (2006.01) |
| ***A61K 8/73*** | (2006.01) |
| ***A61K 8/81*** | (2006.01) |
| ***A61Q 19/10*** | (2006.01) |

(52) U.S. Cl.

CPC .............. *A61K 8/0258* (2013.01); *A61K 8/19* (2013.01); *A61K 8/73* (2013.01); *A61K 8/731* (2013.01); *A61K 8/8129* (2013.01); *A61K 8/8176* (2013.01); *A61Q 19/10* (2013.01)

(58) Field of Classification Search

CPC .......... A61Q 19/00; A61Q 5/00; A61Q 11/00; A61K 8/11; A61K 8/345; A61K 8/342; A61K 8/0258; A61K 8/0216; A61K 2800/63; A61K 2800/10; A61K 8/02

See application file for complete search history.

(56) References Cited

U.S. PATENT DOCUMENTS

| | | | |
|---|---|---|---|
| 2004/0171735 A1 | 9/2004 | Choy et al. | |
| 2008/0021115 A1 | 1/2008 | Ikematsu et al. | |
| 2009/0263342 A1* | 10/2009 | Glenn, Jr. | A61K 8/345 424/70.11 |
| 2019/0192396 A1 | 6/2019 | Lee et al. | |

FOREIGN PATENT DOCUMENTS

| | | |
|---|---|---|
| CN | 104059235 A | 9/2014 |
| EP | 1186286 A1 | 3/2002 |
| EP | 1840113 B1 | 5/2017 |
| KR | 10-2003-0015843 A | 2/2003 |
| KR | 10-2007-0091672 A | 9/2007 |
| KR | 10-1735564 B1 | 5/2017 |
| KR | 10-2018-0021282 A | 3/2018 |
| KR | 10-2018-0021283 A | 3/2018 |
| WO | WO-00/76462 A1 | 12/2000 |

OTHER PUBLICATIONS

International Search Report from corresponding PCT Application No. PCT/KR2020/005198, dated Jul. 24, 2020.

European Search Report from corresponding European Application No. 20795429.8, dated Jul. 25, 2023.

Office Action from corresponding EP Application No. 20795429.8, dated Jan. 13, 2026.

* cited by examiner

*Primary Examiner* — Tracy Liu

(74) *Attorney, Agent, or Firm* — Harness, Dickey & Pierce, P.L.C.

(57) ABSTRACT

The present invention relates to a cosmetic composition for molding, comprising a calcined layered double hydroxide and a polymer and, more specifically, to a cosmetic composition for molding and a preparation method therefor, the cosmetic composition comprising an active ingredient, a calcined layered double hydroxide, a polymer, and a solvent.

14 Claims, 5 Drawing Sheets

COSMETIC COMPOSITION FOR MOLDING, COMPRISING CALCINED LAYERED DOUBLE HYDROXIDE AND POLYMER

CROSS-REFERENCE TO RELATED APPLICATIONS

This application is a national phase application of PCT Application No. PCT/KR2020/005198, filed on Apr. 20, 2020, which claims the benefit and priority to Korean Patent Application No. 10-2019-0047252 filed on Apr. 23, 2019. The entire disclosures of the applications identified in this paragraph are incorporated herein by references.

TECHNICAL FIELD

The present invention relates to a cosmetic composition for molding, comprising a calcined layered double hydroxide and a polymer. More specifically, the present invention relates to cosmetic composition for molding, which comprises an active ingredient, a calcined layered double hydroxide, a polymer and a solvent, and a method for preparing thereof.

BACKGROUND ART

Because of the development of functional materials, various functionalization methods for imparting higher stability to cosmetic raw materials have been widely studied. Specifically, it is well known that light, heat and oxygen in the air seriously reduce the biological activity of functional materials. As such, there is a need to develop a new functionalization technique for stabilizing various cosmetic active ingredients.

As one of such cosmetic active ingredient delivery systems, layered double hydroxide (LDH) is attracting attention. The layered double hydroxide is an inorganic compound with a layered structure, and the shape is layered like the lamellae of the stratum. LDH is basically an inorganic material with structural properties capable of absorbing various anions from small gas molecules such as carbon dioxide to biopolymers such as DNA. In addition, molecules intercalated in the layer can be kept energetically stable by electrostatic interaction with the inorganic layer. Anions have the characteristic of absorbing or releasing by ion exchange. Since the inorganic layer is composed of various compositions ranging from alkali metals to transition metals, it can be used as a precursor material for catalysts, magnetic materials, electronic materials and the like. Recently, a mechanism for self-assembling LDH nanomaterials by the use of specific molecular linkages or a mechanism for controlling the release of anions in the layer in a specific environment by selectively inducing the surface reaction of the inorganic layer has been discovered, so that it is also attracting attention as a sensor or drug delivery material. Specifically, if the electrostatic attraction existing between the layers is chemically minimized, it can be separated into a 1-nm thick nanolayer. This has become a priming powder that explosively increases the applicability of LDH materials, and LDH has been applied to fields such as nanoelectronics, magento-optics, nanosensor, etc. In addition, the LDH nanolayer—which has excellent adsorption capacity for functional organic molecules—is attracting attention as a new bio-encapsulation material based on the development of technologies such as improving the adsorption capacity of cosmetic active ingredients and controlling the release according to chemical environment control. As an example of utilizing LDH, Korean Patent Application Publication No. 10-2018-0109205 discloses a cosmetic composition comprising an extract of fruit of *Dioscorea polystachya* and layered double hydroxide wherein liposomes are mixed with layered double hydroxides and milled to form capsules in which the liposomes are adsorbed between the layers of layered double hydroxide, thereby secondarily stabilizing an extract of fruit of *Dioscorea polystachya*.

Meanwhile, with the development of cosmetics, interest in various visible cosmetics is increasing. Although the efficacy or effect according to active ingredients of cosmetics is also important, there are increasing cases in which consumers purchase after seeing the appearance of the cosmetic product before use. Specifically, various formulations such as essence or cream in a visible capsule formulation are sold, and there are also formulations in which hyaluronic acid, collagen and the like are visible by freeze-drying. According to the changes of times, there is a continuous demand for cosmetics of various shapes that can visually satisfy consumers.

PRIOR DOCUMENT

[Patent Document]

Korean Patent Application Publication No. 10-2018-0109205

SUMMARY

Technical Problem

Accordingly, the technical problem of the present invention is the provision of a cosmetic composition which not only can efficiently deliver an active ingredient into the skin in a stable manner but also can be freely molded into various shapes with excellent moldability.

In addition, another technical problem of the present invention is the provision of a method for effectively preparing the cosmetic composition for molding.

Solution to Problem

To solve the above technical problem, the present invention provides a cosmetic composition for molding, which comprises an active ingredient, a calcined layered double hydroxide, a polymer and a solvent.

In addition, the present invention provides a method for preparing a cosmetic composition for molding comprising: i) calcining a layered double hydroxide at a temperature of 400 to 1,200° C. for 6 to 16 hours and cooling; and ii) dissolving an active ingredient and a polymer in a solvent, mixing the obtained solution with the calcined layered double hydroxide and stirring.

The present invention is described in detail hereinafter.

According to one aspect to the present invention, there is provided a cosmetic composition for molding, which comprises an active ingredient, a calcined layered double hydroxide, a polymer and a solvent.

The cosmetic composition for molding of the present invention comprises an active ingredient preferably in an amount of 0.01 to 50% by weight, more preferably 0.1 to 48% by weight and more preferably 1 to 45% by weight. In cosmetic composition for molding of the present invention, if the amount of the active ingredient is less than 0.01% by weight, the efficacy according to an active ingredient may be weak, and if the amount of an active ingredient is more than 50% by weight, it may be problematic in the molding of the cosmetic composition.

In the present invention, there is no special limitation according to an active ingredient. In the present invention, examples of an active ingredient include, but are not limited to, one or more selected from the group consisting of a moisturizer, a whitening agent, an anti-wrinkle agent, a UV blocking agent, a hair growth promoter, vitamin or a derivative thereof, amino acid or peptide, an anti-inflammatory agent, an acne therapeutic agent, a microbicide, female hormone, a keratolytic agent and a natural product.

Examples of moisturizer include, but are not limited to, creatine, polyglutamic acid, sodium lactate, hydroproline, 2-pyrrolidone-5-carboxyclic acid sodium salt, hyaluronic acid, sodium hyaluronate, ceramide, phytosteryl, cholesterol, sitosterol, pullulan and proteoglycan. Examples of whitening agent include, but are not limited to, arbutin and a derivative thereof, kojic acid, bisabolol, niacinamide, vitamin C and a derivative thereof, placenta and allantoin. Examples of anti-wrinkle agent include, but are not limited to, retinol, retinol derivative, adenosine, licorice extract, red *ginseng* extract and *ginseng* extract. Examples of UV blocking agent include, but are not limited to, benzophenone derivative, para-aminobenzoic acid derivative, methoxycinnamic acid derivative and salicylic acid derivative. There is no special limitation to a hair growth promoter, but it may be preferably a blood circulation promoter and/or a hair follicle stimulant. Examples of blood circulation promoter include, but are not limited to, the extract of *Swertia japonica* Makino, cepharanthin, vitamin E and a derivative thereof and gamma-oryzanol, and examples of hair follicle stimulant include, but are not limited to, *capsicum* tincture, ginger tincture, cantharides tincture and nicotinic acid benzyl ester. Examples of vitamin or a derivative thereof include, but are not limited to, vitamin A (retinol) and a derivative thereof, vitamin B1, vitamin B2, vitamin B6, vitamin E and derivatives thereof, vitamin D, vitamin H, vitamin K, pantothenic acid and derivatives thereof, biotin, panthenol, coenzyme $Q_{10}$ and idebenone. Examples of amino acid or peptide include, but are not limited to, cysteine, methionine, serine, lysine, tryptophan, amino acid extract, epidermal growth factor (EGF), insulin-like growth factor (IGF), fibroblast growth factor (FGF), copper tripeptide-1, tripeptide-29, tripeptide-1, acetyl hexapeptide-8, nicotinoyl tripeptide-35, hexapeptide-12, hexapeptide-9, palmitoyl pentapeptide-4, palmitoyl tetrapeptide-7, palmitoyl tripeptide-29, palmitoyl tripeptide-1, nonapeptide-7, tripeptide-10 citrulline, sh-polypeptide-15, palmitoyl tripeptide-5, diaminopropionoyl tripeptide-33 and r-spider polypeptide-1. Examples of anti-inflammatory agent include, but are not limited to, beta-glycyrrhetinic acid, glycyrrhetinic acid derivative, aminocaproic acid, hydrocortisone, β-glucan and licorice. Examples of acne therapeutic agent include, but are not limited to, estradiol, estrogen, ethinyl estradiol, triclosan and azelaic acid. Examples of microbicide include, but are not limited to, benzalkonium chloride, benzethonium chloride and halocalban. There is no special limitation to female hormone, but it may be preferably estrogen. As estrogen, it may be preferably estradiol, ethinyl estradiol or isoflavone which is a phytoestrogen. Examples of keratolytic agent include, but are not limited to, sulfur, salicylic acid, AHA, BHA and resorcin. Examples of the extract of natural product or an ingredient obtained therefrom include, but are not limited to, the extract of Japanese witch-hazel, *Lamium album* var. *barbatum, Hedyotis diffuse, Rheum palmatum*, licorice, aloe, chamomile, rose hip, horse chestnut, *ginseng, Luffa aegyptiaca*, cucumber, laver, sea mustard, *Dioscorea batatas*, snail and fruit of *Dioscorea polystachya*, or hinokitiol and beta-carotene. In addition, yeast extract, collagen, elastin, DHA, EPA, flavor ingredient and the like may be used.

The cosmetic composition for molding of the present invention comprises a calcined layered double hydroxide (LDH) preferably in an amount of 10 to 60% by weight, more preferably 15 to 55% by weight and more preferably 20 to 50% by weight. In the cosmetic composition for molding of the present invention, if the amount of calcined layered double hydroxide is less than 10% by weight, the efficacy of delivering an active ingredient into the skin may be lowered, and if the amount of calcined layered double hydroxide is more than 60% by weight, it may be problematic in the molding of the cosmetic composition.

In the present invention, the composition of LDH can be represented by the formula, $[M^{2+}{}_{1-x}M^{3+}{}_{x}(OH)_2]^{x+}(A^{n-})_{x/n}\cdot mH_2O$. In the formula, $M^{2+}$ and $M^{3+}$ are metal cations which locate octahedral sites of brucite; $A^{n-}$ represents anions located between layers; $M^{2+}=Ca^{2+}$, $Mg^{2+}$, $Zn^{2+}$, $Ni^{2+}$, $Mn^{2+}$, $Co^{2+}$, $Fe^{2+}$ and the like; $M^{3+}=Al^{3+}$, $Cr^{3+}$, $Mn^{3+}$, $Fe^{3+}$, $Ga^{3+}$, $Co^{3+}$, $Ni^{3+}$ and the like; $A^{n-}$ is $OH^-$, $F^-$, $Cl^-$, $Br^-$, $I^-$, $NO_{3^-}$, $CO_3{}^{2-}$, $SO_4{}^{2-}$ and the like; $0.2 \le x \le 0.33$ in a fixed-composition phase; n is 1 or 2; and m is usually between 0.5 and 4.

The anions located in the interlayer regions of LDH structure can be replaced easily, so that even biomolecules such as collagen tripeptide and solid nanoparticle containing Ag, Au, Pt and the like as well as halogen ion and biomacromolecules having negative charge such as DNA can be intercalated. The basic layered structure of LDH and examples of available metal cations and anions are represented in FIG. 1. The preparation of LDH may be carried out according to the methods known in this technical field such as a hydrothermal method, a convection circulation method, an ultrasonic method and the like.

In the present invention, the calcination of LDH may be carried out according to the methods known in this technical field, there is no specific limitation thereto. In one embodiment according to the present invention, the calcination of LDH is carried out by heating LDH in a furnace at a temperature of about 400 to 1,200° C., more preferably about 500 to 1,100° C., for about 6 to 16 hours, more preferably about 8 to 14 hours.

In one embodiment according to the present invention, the surface functionalization and surface modification may be conducted on the surface of metal hydroxide of LDH with various materials. For example, the surface of LDH may be modified with materials such as dodecyl sulfate, stearate and the like.

The cosmetic composition for molding of the present invention comprises a polymer preferably in an amount of 0.5 to 20% by weight, more preferably 1 to 18% by weight and more preferably 2 to 15% by weight. In the cosmetic composition for molding of the present invention, if the amount of polymer is less than 0.5% by weight or more than 20% by weight, it may be problematic in the molding of the cosmetic composition.

In the present invention, for example, the polymer may be one or more selected from cellulose, methylcellulose, hydroxyethyl cellulose, microcrystalline cellulose, nanocellulose, starch, polymethyl methacrylate, polyacrylic acid, acrylates/C10-30 alkyl acrylate crosspolymer, polyvinyl alcohol, polyvinylpyrrolidone, polyglycolide, xanthan gum, acacia gum, guar gum, carrageenan gum, gellan gum, karaya gum, locust bean gum, hyaluronic acid, pullulan, sodium alginate, chitosan, agar, gelatin and collagen, but is not limited thereto.

The cosmetic composition for molding of the present invention comprises a solvent preferably in an amount of 10 to 60% by weight, more preferably 15 to 55% by weight and more preferably 20 to 50% by weight. In the cosmetic composition for molding of the present invention, if the amount of solvent is less than 10% by weight or more than 60% by weight, it may be problematic in the molding of the cosmetic composition.

In the present invention, examples of the solvent include, but are not limited to, water, glycerin, propylene glycol, butylene glycol, diglycerin, dipropylene glycol and a mixture thereof.

The cosmetic composition for molding of the present invention may further comprise ingredients such as a stabilizer, an antioxidant, a lubricant and the like, if necessary.

According to another aspect to the present invention, there is provided a method for preparing a cosmetic composition for molding comprising: i) calcining a layered double hydroxide at a temperature of 400 to 1,200° C. for 6 to 16 hours and cooling; and ii) dissolving an active ingredient and a polymer in a solvent, mixing the obtained solution with the calcined layered double hydroxide and stirring.

In the step (i) of the above preparation method, the composition of the layered double hydroxide is the same as defined above, and the calcination is preferably carried out at a temperature of 500 to 1,100° C. for 8 to 14 hours.

In the step (ii) of the above preparation method, there is no special limitation according to an active ingredient, and examples of an active ingredient include, but are not limited to, one or more selected from the group consisting of a moisturizer, a whitening agent, an anti-wrinkle agent, a UV blocking agent, a hair growth promoter, vitamin or a derivative thereof, amino acid or peptide, an anti-inflammatory agent, an acne therapeutic agent, a microbicide, female hormone, a keratolytic agent and a natural product.

In the step (ii) of the above preparation method, for example, the polymer may be one or more selected from the group consisting of cellulose, methylcellulose, hydroxyethyl cellulose, microcrystalline cellulose, nanocellulose, starch, polymethyl methacrylate, polyacrylic acid, acrylates/C10-30 alkyl acrylate crosspolymer, polyvinyl alcohol, polyvinylpyrrolidone, polyglycolide, xanthan gum, acacia gum, guar gum, carrageenan gum, gellan gum, karaya gum, locust bean gum, hyaluronic acid, pullulan, sodium alginate, chitosan, agar, gelatin and collagen, but is not limited thereto.

In the step (ii) of the above preparation method, examples of the solvent include, but are not limited to, water, glycerin, propylene glycol, butylene glycol, diglycerin, dipropylene glycol and a mixture thereof.

In the step (ii) of the above preparation method, the weight ratio of the active ingredient, the polymer, the solvent and the calcined layered double hydroxide is preferably 0.01 to 50% by weight, 0.5 to 20% by weight, 10 to 60% by weight and 10 to 60% by weight; more preferably 0.1 to 48% by weight, 1 to 18% by weight, 15 to 55% by weight and 15 to 55% by weight; and more preferably 1 to 45% by weight, 2 to 15% by weight, 20 to 50% by weight and 20 to 50% by weight, respectively.

The molding of the cosmetic composition for molding according to the present invention may be carried out in accordance with the methods known in this technical field to form various shapes (round ball, cubic, shell shape, flower shape, star shape, heart shape, alphabet shape, general plate shape, etc.), and there is no specific limitation thereto. For example, various shapes can be prepared by putting the cosmetic composition for molding according to the present invention into a mold of a desired shape through an input unit, performing compression, followed by separating and drying.

In addition, the cosmetic composition for molding according to the present invention can provide cosmetics in various formulations such as cleansing, a foaming agent for bubble bath, essence, body wash and the like depending on an active ingredient.

Advantageous Effects of Invention

A cosmetic composition for molding of the present invention not only can efficiently deliver an active ingredient into the skin in a stable manner but also can provide cosmetics that are aesthetically superior as they can have various shapes with excellent moldability and are convenient to store or carry.

DETAILED DESCRIPTION

Figure 1:
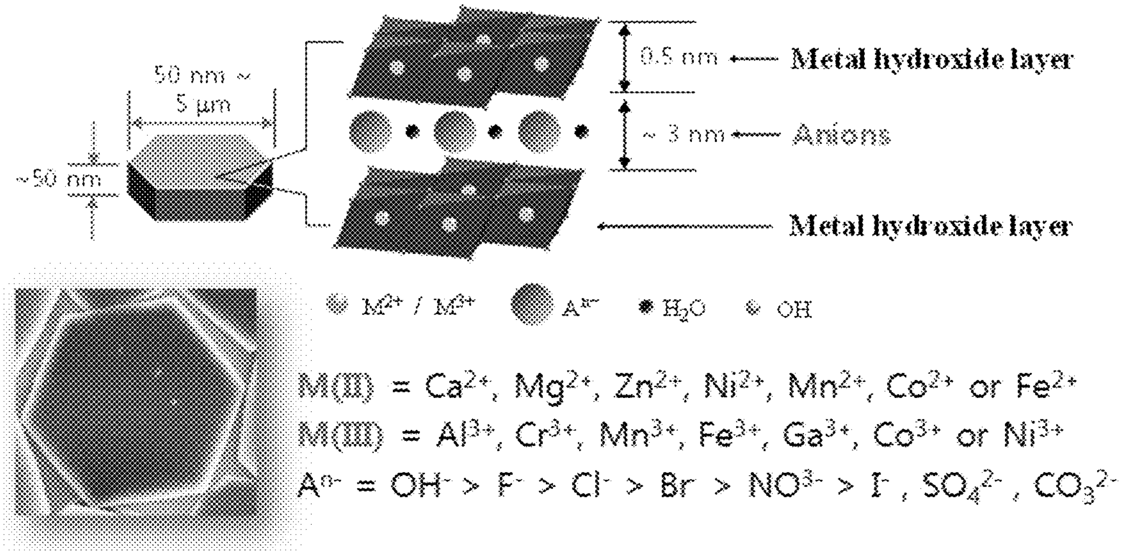
FIG. 1 is a scheme representing the layered structure and composition of layered double hydroxide (LDH).

Hereinafter, the present invention is explained in more detail with the following examples. However, it must be understood that the protection scope of the present invention is not limited to the examples.

Preparation Example 1: Synthesis of Aluminum/Magnesium Hydroxide Stearate

A commercially available product was purchased from Taesan Chemical (Korea).

Preparation Example 2: Synthesis of ZnAl-LDH

ZnAl-LDH containing carbonate ion was synthesized by co-precipitation as follows. 1 M $Na_2CO_3$ solution was slowly added to the mixed solution of 0.2 M $Zn(NO_3)_2$ and 0.1 M $Al(NO_3)_3$ until the final pH became about 7.0. The mixed solution was kept in an about 70° C. oven for a day, filtered, washed with distilled water and ethanol, and dried by the use of a vacuum pump. The formula of the synthesized c-LDH is as follows: $[Zn_4Al_2(OH)_{12}]CO_3 \cdot xH_2O$.

Preparation Example 3: Synthesis of MgAl-LDH

MgAl-LDH containing carbonate ion was synthesized by co-precipitation as follows. 1 M $Na_2CO_3$ solution was slowly added to the mixed solution of 0.2 M $Mg(NO_3)_2$ and 0.1 M $Al(NO_3)_3$ until the final pH became about 7.0. The mixed solution was kept in an about 70° C. oven for a day, filtered, washed with distilled water and ethanol, and dried by the use of a vacuum pump. The formula of the synthesized c-LDH is as follows: $[Mg_4Al_2(OH)_{12}]CO_3 \cdot xH_2O$.

Preparation Example 4: Synthesis of Aluminum/Magnesium Silicate

A commercially available product was purchased from BYK-Chemie GmbH (Germany).

Example 1: Preparation of Composition for Molding Containing Vitamin

According to the constitutional composition of Table 1, aluminum/magnesium hydroxide stearate obtained in Preparation Example 1 was heated in a furnace at a temperature of 1,000° C. for 12 hours and then cooled to 20° C. After dissolving retinol as an active ingredient and chitosan as a polymer in water, the calcined aluminum/magnesium hydroxide stearate was mixed thereto and stirred with a mixer for 20 minutes to obtain a composition for molding.

TABLE 1

| Ingredient | Content (% by weight) |
|---|---|
| LDH of Preparation Example 1 | 40 |
| Chitosan | 4 |
| Retinol | 20 |
| Distilled water | 36 |
| Total amount | 100 |

Example 2: Preparation of Composition for Molding Containing Peptide

A composition for molding was prepared by the same method as described in Example 1 except that the ingredients and constitutional composition of Table 2 were used.

TABLE 2

| Ingredient | Content (% by weight) |
|---|---|
| LDH of Preparation Example 2 | 40 |
| Acrylates/C10-30 alkyl acrylate | 4 |
| crosspolymer | 20 |
| Copper peptide | 36 |
| Distilled water | |
| Total amount | 100 |

Example 3: Preparation of Composition for Molding Containing Whitening Agent A composition for molding was prepared by the same method as described in Example 1 except that the ingredients and constitutional composition of Table 3 were used.

TABLE 3

| Ingredient | Content (% by weight) |
|---|---|
| LDH of Preparation Example 3 | 40 |
| Polyvinyl alcohol | 4 |
| Arbutin | 20 |
| Propylene glycol | 36 |
| Total amount | 100 |

Example 4: Preparation of Composition for Molding Containing Natural Product A composition for molding was prepared by the same method as described in Example 1 except that the ingredients and constitutional composition of Table 4 were used.

TABLE 4

| Ingredient | Content (% by weight) |
|---|---|
| LDH of Preparation Example 4 | 40 |
| Starch | 4 |
| Redstem wormwood extract | 20 |
| Glycerin | 36 |
| Total amount | 100 |

Example 5: Preparation of Composition for Molding in Formulation of Cleansing 1

A composition for molding was prepared by the same method as described in Example 1 except that the ingredients and constitutional composition of Table 5 were used.

TABLE 5

| Ingredient | Content (% by weight) |
|---|---|
| LDH of Preparation Example 2 | 40 |
| Methylcellulose | 5 |
| Sodium stearoyl glutamate | 8 |
| Disodium stearoyl glutamate | 8 |
| Sodium lauroyl glutamate | 7 |
| PEG-400 | 8 |
| Glycerin | 24 |
| Total amount | 100 |

Example 6: Preparation of Composition for Molding in Formulation of Cleansing 2

A composition for molding was prepared by the same method as described in Example 1 except that the ingredients and constitutional composition of Table 6 were used.

TABLE 6

| Ingredient | Content (% by weight) |
|---|---|
| LDH of Preparation Example 1 | 38 |
| Microcrystalline cellulose | 7 |
| Sodium lauryl glucose carboxylate | 8 |
| Sodium methyl cocoyl taurate | 8 |
| Sodium lauroyl sarcosinate | 7 |
| Betain | 8 |
| Distilled water | 24 |
| Total amount | 100 |

Example 7: Preparation of Composition for Molding in Formulation of Cleansing 3

A composition for molding was prepared by the same method as described in Example 1 except that the ingredients and constitutional composition of Table 7 were used.

TABLE 7

| Ingredient | Content (% by weight) |
|---|---|
| LDH of Preparation Example 3 | 39 |
| Polyvinylpyrrolidone | 5 |
| Sodium laures sulfate | 8 |
| Sodium cocoyl glutamate | 8 |
| Sodium decyl sulfate | 8 |
| PEG-400 | 8 |
| Dipropylene glycol | 24 |
| Total amount | 100 |

Example 8: Preparation of Composition for Molding in Formulation of Cleansing 3

A composition for molding was prepared by the same method as described in Example 1 except that the ingredients and constitutional composition of Table 8 were used.

TABLE 8

| Ingredient | Content (% by weight) |
|---|---|
| LDH of Preparation Example 4 | 28 |
| Polyvinyl alcohol | 12 |
| Sodium bicarbonate | 7 |
| Mannitol | 14 |
| Trehalose | 7 |
| Distilled water | 32 |
| Total amount | 100 |

Example 9: Preparation of Composition for Molding in Formulation of Foaming Agent for Bubble Bath A composition for molding was prepared by the same method as described in Example 1 except that the ingredients and constitutional composition of Table 9 were used.

TABLE 9

| Ingredient | Content (% by weight) |
|---|---|
| LDH of Preparation Example 1 | 39 |
| Polyvinylpyrrolidone | 5 |
| Citric acid | 8 |
| Sodium bicarbonate | 8 |
| PEG-6000 | 8 |
| PEG-4000 | 8 |
| Glycerin | 24 |
| Total amount | 100 |

Example 10: Preparation of Composition for Molding in Formulation of Essence

A composition for molding was prepared by the same method as described in Example 1 except that the ingredients and constitutional composition of Table 10 were used.

TABLE 10

| Ingredient | Content (% by weight) |
|---|---|
| LDH of Preparation Example 3 | 35 |
| Hydroxyethyl cellulose | 6 |
| Mannitol | 18 |
| Trehalose | 5 |
| Collagen | 8 |
| Hyaluronic acid | 7 |
| Distilled water | 21 |
| Total amount | 100 |

Example 11: Molding of Composition for Molding

Figure 2:
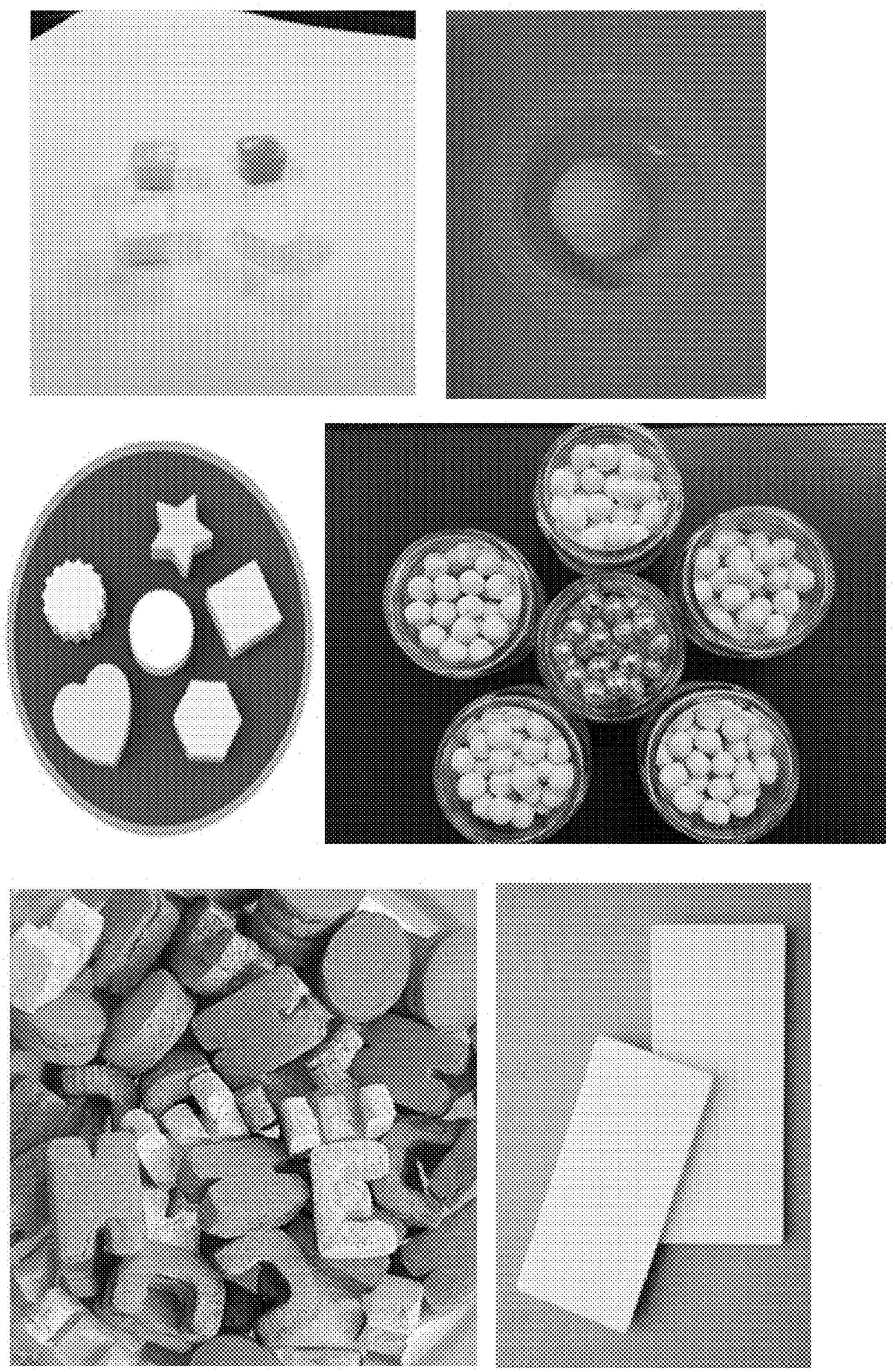
FIG. 2 is photographs taken after molding the cosmetic composition for molding of the present invention in various shapes in Example 11.

The molding compositions obtained in Examples 1 to 10 were put into a mold in various shapes to be molded, and then dried in a drying oven at a temperature of 50 to 60° C. for 6 hours (FIG. 2).

Comparative Example

Figure 3:
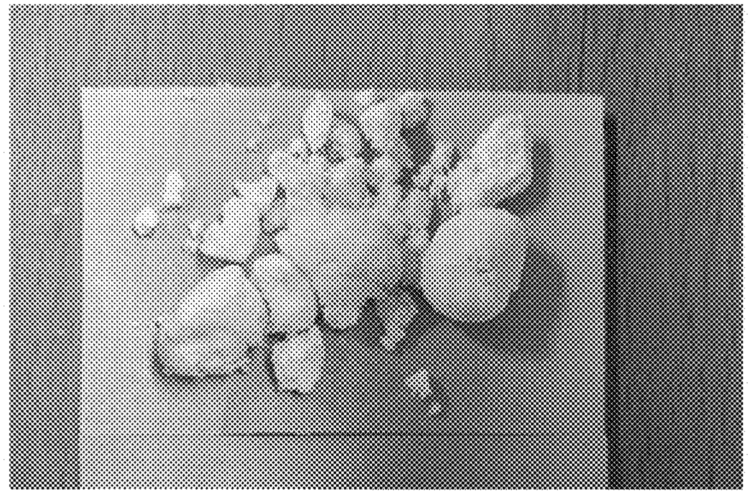
FIG. 3 is a photograph taken after molding the cosmetic composition for molding of the Comparative Example.

A composition for molding containing vitamin was prepared in the same manner as in Example 1 except that the layered double hydroxide which did not undergo a calcination step was used, and then the obtained composition for molding was molded (FIG. 3).

Experimental Example 1: Measurement of Zeta Potential

Figure 4:
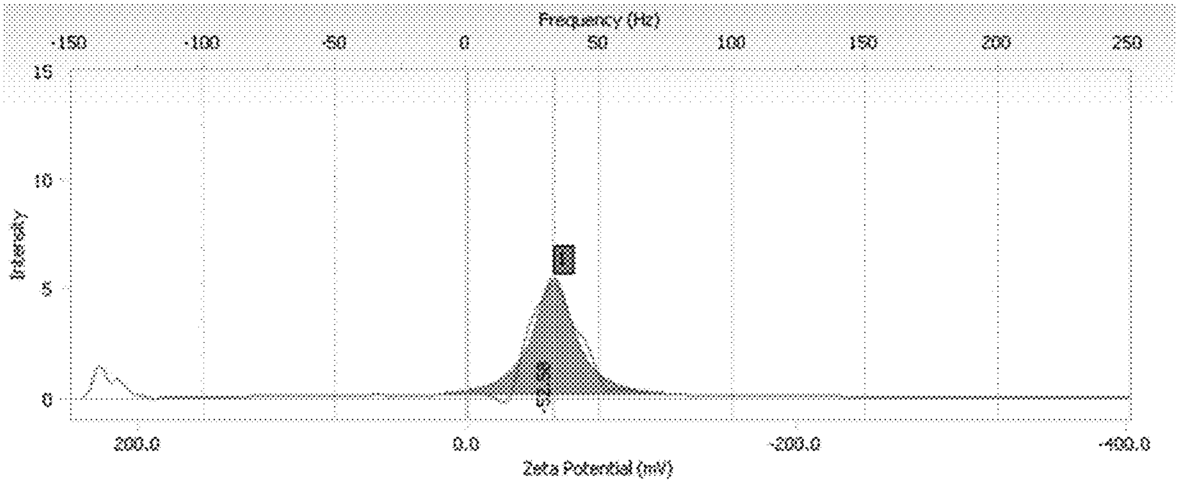
FIG. 4 is a result of measuring zeta potential of the composition prepared in Example 1 by the use of Photal, ELS-Z.

The zeta potential of the composition prepared in Example 1 was measured by the use of Photal, ELS-Z, and it can be known that the zeta potential is −52.58 mV (FIG. 4).

Experimental Example 2: Measurement of Stability

Figure 5:
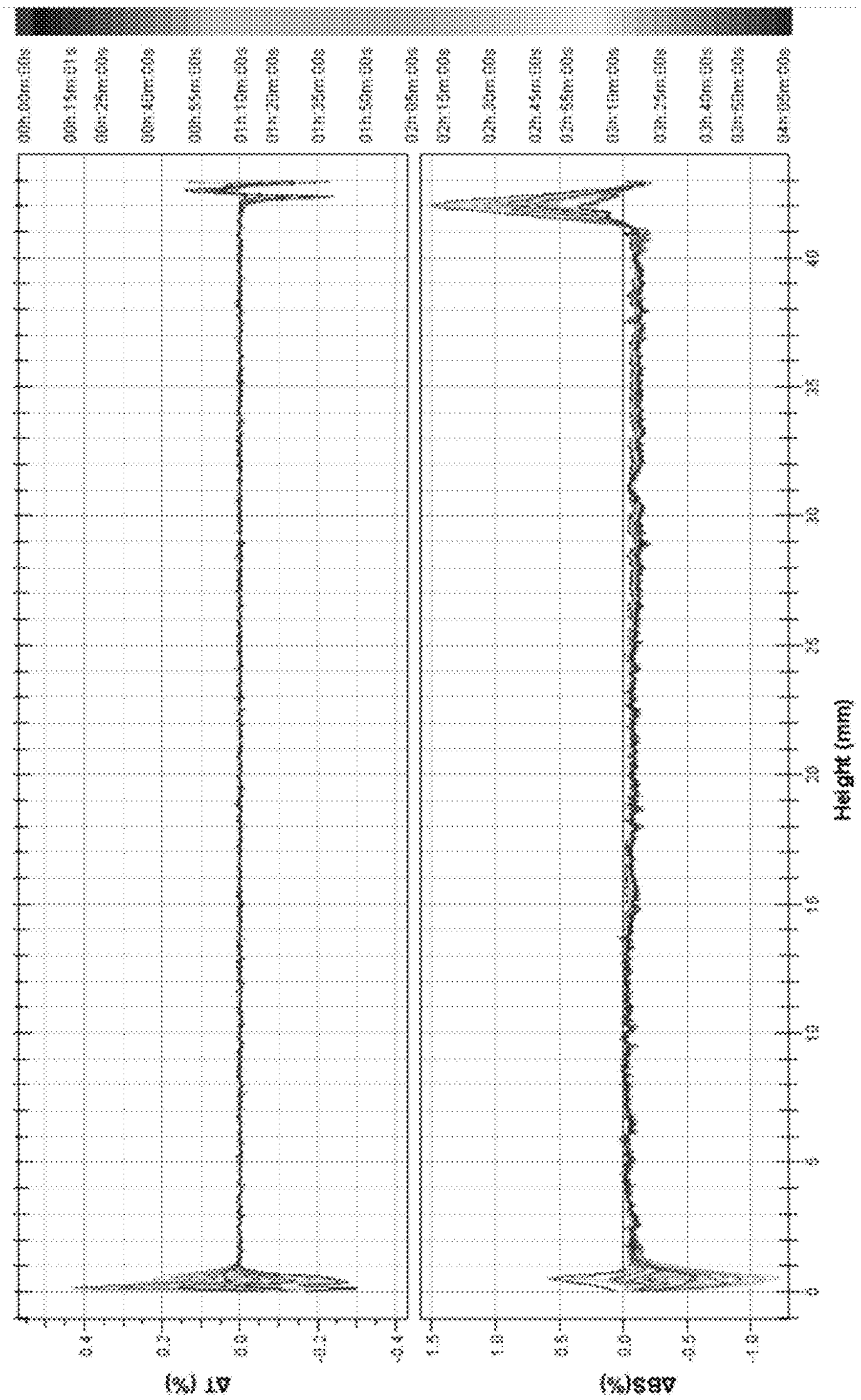
FIG. 5 is a result of measuring the stability of the composition prepared in Example 1 by the use of Turbiscan.

The stability of the composition prepared in Example 1 was measured by the use of Turbiscan. As a result, the stability of the composition was confirmed since there was little change in ΔT, ΔBS (FIG. 5).

Experimental Example 3: Cryo-Electron Microscopy

Figure 6:
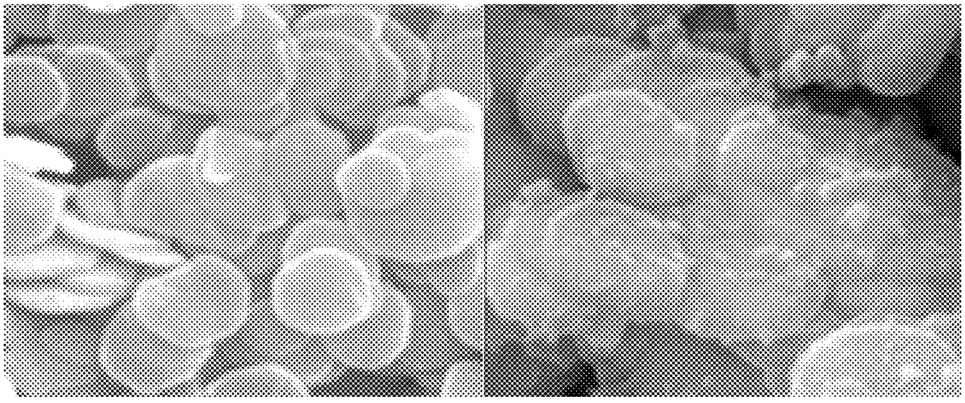
FIG. 6 is a cryo-electron microscopy photograph of the composition prepared in Example 1.

Photographs of the composition prepared in Example 1 were taken by the use of a cryo-electron microscope (JEM 1010, JEOL Ltd., Japan) (FIG. 6).

Experimental Example 4: Test for Effect on Promoting Transdermal Absorption

The artificial skin, Strat-M® Membrane (Transdermal Diffusion Test Model) was mounted to a Franz-type diffusion cell (Transdermal Semi-Auto Diffusion Cell, LOGAN Instruments, USA). 50 mM phosphate buffer (pH 7.4, 0.1M NaCl) was added to a receptor cell (5 ml) of the Franz-type diffusion cell. A diffusion cell was then mixed and diffused at 600 rpm, 32° C., and 50 µl of the composition of Example 1 was added to a donor cell. Absorption and diffusion were carried out according to the predetermined time, and the area of the skin where the absorption and diffusion were carried out was 0.64 $cm^2$. After finishing the absorption and diffusion of the active ingredient, the residues—which were not absorbed and remained on the skin—were cleaned with dried Kimwipes™ or 10 ml of ethanol. The skin in which the active ingredient was absorbed and diffused was homogenized by the use of a tip-type homogenizer, and retinol absorbed into the skin was then extracted with 4 ml of dichloromethane. The extract was then filtrated with a 0.45 μm nylon membrane filter. The content of retinol was measured by high-performance liquid chromatography with the following conditions. As a result, it was confirmed that retinol can be efficiently delivered into the skin since the transdermal absorption is 0.364 μg.

Column: C18 (4.6×200 mm, 5 μm)
Mobile phase: methanol:hexane=2:1
Flow rate: 0.8 ml/min
Detector: UV 275 nm

What is claimed is:

1. A cosmetic composition, which comprises 0.01 to 50% by weight of an active ingredient, 10 to 60% by weight of a calcined layered double hydroxide, 0.5 to 20% by weight of a polymer and 10 to 60% by weight of a solvent;

wherein the layered double hydroxide has the following formula:

$$[M^{2+}_{1-x}M^{3+}_x(OH)_2]^{x+}(A^{n-})_{x/n}\cdot mH_2O$$

wherein
$M^{2+}$ and $M^{3+}$ are metal cations,
$A^{n-}$ is anion,
$0.2 \le x \le 0.33$,
n is 1 or 2, and
m is 0.5 to 4; and wherein the polymer is one or more selected from the group consisting of cellulose, methylcellulose, hydroxyethyl cellulose, microcrystalline cellulose, nanocellulose, starch, polymethyl methacrylate, polyacrylic acid, acrylates/C10-30 alkyl acrylate crosspolymer, polyvinyl alcohol, polyvinylpyrrolidone, polyglycolide, xanthan gum, acacia gum, guar gum, carrageenan gum, gellan gum, karaya gum, locust bean gum, hyaluronic acid, pullulan, sodium alginate, chitosan, agar, gelatin, and collagen, wherein $M^{2+}$ is $Ca^{2+}$, $Mg^{2+}$, $Zn^{2+}$, $Ni^{2+}$, $Mn^{2+}$, $Co^{2+}$ or $Fe^{2+}$; $M^{3+}$ is $Al^{3+}$, $Cr^{3+}$, $Mn^{3+}$, $Fe^{3+}$, $Ga^{3+}$, $Co^{3+}$ or $Ni^{3+}$; and $A^{n-}$ is $OH^-$, $F^-$, $Cl^-$, $Br^-$, $I^-$, $NO_3^-$, $CO_3^{2-}$ or $SO_4^{2-}$;

wherein the cosmetic composition is molded to form a shape, and wherein the calcined layered double hydroxide enables molding of the cosmetic composition to form a shape.

2. The cosmetic composition according to claim 1, which comprises 0.1 to 48% by weight of active ingredient, 15 to 55% by weight of calcined layered double hydroxide, 1 to 18% by weight of polymer and 15 to 55% by weight of solvent.

3. The cosmetic composition according to claim 2, which comprises 1 to 45% by weight of active ingredient, 20 to 50% by weight of calcined layered double hydroxide, 2 to 15% by weight of polymer and 20 to 50% by weight of solvent.

4. The cosmetic composition according to claim 1, wherein the active ingredient is one or more selected from the group consisting of a moisturizer, a whitening agent, an anti-wrinkle agent, a UV blocking agent, a hair growth promoter, vitamin or a derivative thereof, amino acid or peptide, an anti-inflammatory agent, an acne therapeutic agent, a microbicide, female hormone, a keratolytic agent and a natural product.

5. The cosmetic composition according to claim 1, wherein the calcined layered double hydroxide is calcined at a temperature of 400 to 1,200° C.

6. The cosmetic composition according to claim 5, wherein the calcined layered double hydroxide is calcined at a temperature of 500 to 1,100° C.

7. The cosmetic composition according to claim 1, wherein the calcined layered double hydroxide is calcined for 6 to 16 hours.

8. The cosmetic composition according to claim 7, wherein the calcined layered double hydroxide is calcined for 8 to 14 hours.

9. The cosmetic composition according to claim 1, wherein the solvent is selected from water, glycerin, propylene glycol, butylene glycol, diglycerin, dipropylene glycol and a mixture thereof.

10. A method for preparing a cosmetic composition comprising:

i) calcining a layered double hydroxide at a temperature of 400 to 1,200° C. for 6 to 16 hours and cooling; and
ii) dissolving an active ingredient and a polymer in a solvent, mixing the obtained solution with the calcined layered double hydroxide and stirring;

wherein the layered double hydroxide has the following formula:

$$[M^{2+}_{1-x}M^{3+}_x(OH)_2]^{x+}(A^{n-})_{x/n}\cdot mH_2O$$

wherein
$M^{2+}$ and $M^{3+}$ are metal cations,
$A^{n-}$ is anion,
$0.2 \le x \le 0.33$,
n is 1 or 2, and
m is 0.5 to 4; and wherein the polymer is one or more selected from the group consisting of cellulose, methylcellulose, hydroxyethyl cellulose, microcrystalline cellulose, nanocellulose, starch, polymethyl methacrylate, polyacrylic acid, acrylates/C10-30 alkyl acrylate crosspolymer, polyvinyl alcohol, polyvinylpyrrolidone, polyglycolide, xanthan gum, acacia gum, guar gum, carrageenan gum, gellan gum, karaya gum, locust bean gum, hyaluronic acid, pullulan, sodium alginate, chitosan, agar, gelatin and collagen;

wherein $M^{2+}$ is $Ca^{2+}$, $Mg^{2+}$, $Zn^{2+}$, $Ni^{2+}$, $Mn^{2+}$, $Co^{2+}$ or $Fe^{2+}$; $M^{3+}$ is $Al^{3+}$, $Cr^{3+}$, $Mn^{3+}$, $Fe^{3+}$, $Ga^{3+}$, $Co^{3+}$ or $Ni^{3+}$; and $A^{n-}$ is $OH^-$, $F^-$, $Cl^-$, $Br^-$, $I^-$, $NO_3^-$, $CO_3^{2-}$ or $SO_4^{2-}$; and wherein the weight ratio of the active ingredient, the polymer, the solvent and the calcined layered double hydroxide in step (ii) is 0.01 to 50% by weight, 0.5 to 20% by weight, 10 to 60% by weight and 10 to 60% by weight, respectively, wherein the cosmetic composition is molded to form a shape, and wherein the calcined layered double hydroxide enables molding of the cosmetic composition to form a shape.

11. The method for preparing a cosmetic composition according to claim 10, wherein the layered double hydroxide is calcined at a temperature of 500 to 1,100° C.

12. The method for preparing a cosmetic composition according to claim 10, wherein the layered double hydroxide is calcined for 8 to 14 hours.

13. The method for preparing a cosmetic composition according to claim 10, wherein the active ingredient is one or more selected from the group consisting of a moisturizer, a whitening agent, an anti-wrinkle agent, a UV blocking agent, a hair growth promoter, vitamin or a derivative thereof, amino acid or peptide, an anti-inflammatory agent, an acne therapeutic agent, a microbicide, female hormone, a keratolytic agent and a natural product.

14. The method for preparing a cosmetic composition according to claim 10, wherein the solvent is selected from water, glycerin, propylene glycol, butylene glycol, diglycerin, dipropylene glycol and a mixture thereof.

* * * * *